US012220446B2

(12) United States Patent
Zhang

(10) Patent No.: US 12,220,446 B2
(45) Date of Patent: Feb. 11, 2025

(54) USE OF UPSTREAM OPEN READING FRAME 45aa-uORF NUCLEOTIDE SEQUENCE OF PTEN GENE AND POLYPEPTIDE CODED BY 45aa-uORF

(71) Applicant: THE FIRST AFFILIATED HOSPITAL, SUN YAT-SEN UNIVERSITY, Guangdong (CN)

(72) Inventor: Nu Zhang, Guangdong (CN)

(73) Assignee: THE FIRST AFFILIATED HOSPITAL, SUN YAT-SEN UNIVERSITY, Guangdong (CN)

( * ) Notice: Subject to any disclaimer, the term of this patent is extended or adjusted under 35 U.S.C. 154(b) by 1464 days.

(21) Appl. No.: 16/620,154

(22) PCT Filed: Jun. 8, 2018

(86) PCT No.: PCT/CN2018/090520
§ 371 (c)(1),
(2) Date: Dec. 6, 2019

(87) PCT Pub. No.: WO2018/224044
PCT Pub. Date: Dec. 13, 2018

(65) Prior Publication Data
US 2020/0138915 A1 May 7, 2020

(30) Foreign Application Priority Data
Jun. 8, 2017 (CN) .......................... 201710429319.X

(51) Int. Cl.
C12N 15/55 (2006.01)
A61K 31/713 (2006.01)
A61K 38/17 (2006.01)
A61K 38/46 (2006.01)
A61K 48/00 (2006.01)
C07K 14/435 (2006.01)
C12N 9/16 (2006.01)
C12Q 1/68 (2018.01)
C12Q 1/6886 (2018.01)
G01N 33/574 (2006.01)

(52) U.S. Cl.
CPC .......... A61K 38/465 (2013.01); A61K 31/713 (2013.01); A61K 38/1703 (2013.01); A61K 48/00 (2013.01); C07K 14/435 (2013.01); C12Q 1/6886 (2013.01); C12Y 301/03067 (2013.01); G01N 33/57496 (2013.01); C12Q 2600/158 (2013.01); G01N 2333/916 (2013.01)

(58) Field of Classification Search
CPC .. A61K 31/713; A61K 38/1703; A61K 48/00; C07K 14/435; C12Q 2600/158
See application file for complete search history.

(56) References Cited

U.S. PATENT DOCUMENTS

2004/0142395 A1 7/2004 Durden
2012/0039861 A1 2/2012 Parsons

FOREIGN PATENT DOCUMENTS

| CN | 1837374 A | 9/2006 |
| CN | 101988091 A | 3/2011 |
| CN | 102387810 A | 3/2012 |
| CN | 104178488 A | 12/2014 |
| WO | 1998034624 A1 | 8/1998 |
| WO | 2010065940 A1 | 6/2010 |

OTHER PUBLICATIONS

National Institute of Cancer—understanding and related topics, accessed Aug. 21, 2014 at URL: cancer.gov/cancertopics/understandingcancer, 63 pages (Year: 2014).*
Merck Manuals Lung Carcinoma accessed Mar. 12, 2017 at URL merckmanuals.com/professional/pulmonary-disorders/tumors-of-the-lungs/lung-carcinoma, 18 pages (Year: 2017).*
Merck Manual Colorectal Cancer accessed Aug. 21, 2014 at URL merckmanuals.com/home/digestive_disorders/tumors_of_the_digestive_system/colorectal_cancer.htm, 5 pages (Year: 2014).*
Renal cell carcinoma, accessed Mar. 12, 2017 at URL merckmanuals.com/professional/genitourinary-disorders/genitourinary-cancer/renal-cell-carcinoma, 6 pages (Year: 2017).*
Thyroid cancer accessed Mar. 12, 2017 at URL www.merckmanuals.com/professional/endocrine-and-metabolic-disorders/thyroid-disorders/thyroid-cancers, 4 pages (Year: 2017).*
Merck Manual Bladder Cancer accessed Aug. 21, 2014 at URL: merckmanuals.com/home/kidney_and_urinary_tract_disorders/cancers_of_the_kidney_and_genitourinary_tract/bladder_cancer.html, 2 pages (Year: 2014).*
Merck Manuals Brain Tumors accessed Aug. 21, 2014 at URL merckmanuals.com/home/brain_spinal_cord_and_nerve_disorders/ (Year: 2014).*
Bowie et al, "Deciphering the message in protein sequences: tolerance to amino acid substitutions," Science 247:1306-1310 (1990)) (Year: 1990).*
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol. 111:2129-2138 (1990) (Year: 1990).*

(Continued)

Primary Examiner — Julie Ha
Assistant Examiner — Kristina M Hellman
(74) Attorney, Agent, or Firm — Eventide Law LLC

(57) ABSTRACT

Provided are an upstream Open Reading Frame (uORF) of a Phosphatase and Tensin homolog (PTEN) gene and a protein coded by the uORF. A potential ORF of 138 bases (45aa-uORF) in the 5'UTR of the PTEN, coding an oligopeptide of 45 amino acids (named PTEN-45aa) plays an important role in the development and progression progress of tumors. Further provided are a new diagnostic and therapeutic method and a drug screening platform for PTEN expression regulation related diseases, in particular neuroglioma. Also provided is a polypeptide for treatment of PTEN expression regulation related diseases.

3 Claims, 5 Drawing Sheets
Specification includes a Sequence Listing.

(56) References Cited

OTHER PUBLICATIONS

Merck Manual Breast Cancer accessed Aug. 21, 2014 at URL: merckmanuals.com/home/womens_health_issues/breast_disorders/breast_cancer, 19 pages (Year: 2014).*
Brito et al, "Focus on PTEN regulation," Front Oncol. 5:1-15 (Jul. 2015) (Year: 2015).*
First Office Action of corresponding CN application (CN201710429319.X) Apr. 2, 2021, including English translation.
Tzani, et al., "Systematic analysis of the PTEN 5' leader identifies a major AUU initiated proteoform", Open Biology, vol. 6:150203; pp. 1-13, and supplemental pp. 1-14, May 25, 2016.
International Search Report of PCT Application No. PCT/CN2018/090520 dated Sep. 13, 2018.
Tzani, et al., "Systematic analysis of the PTEN 5' leader identifies a major AUU initiated proteoform", Open Biology, vol. 6:150203; pp. 1-13, May 25, 2016.
Han et al., "Regulation of constitutive expression of mouse PTEN by the 5'-untranslated region", Oncogene, vol. 22, pp. 5325-5337, Dec. 31, 2003.
Zhang et al., "A PTEN translational isoform has PTEN-like activity", Chinese Journal of Cancer Research, vol. 27, No. 5, pp. 524-532, Dec. 31, 2015.
Calvo et al., "Upstream open reading frames cause widespread reduction of protein expression and are polymorphic among humans", PNAS, vol. 106, No. 18, pp. 7507-7512, May 5, 2009.

\* cited by examiner

SEQUENCE LISTING

<160> NUMBER OF SEQ ID NOS: 13

<210> SEQ ID NO 1
<211> LENGTH: 138
<212> TYPE: DNA
<213> ORGANISM: Homo sapiens

<400> SEQUENCE: 1
atgagagacg gcggcggccg cggcccggag cccctctcag cgcctgtgag cagccgcggg      60
ggcagcgccc tcggggagcc ggccggcctg cggcggcggc agcggcggcg tttctcgcct     120
cctcttcgtc ttttctaa                                                   138

<210> SEQ ID NO 2
<211> LENGTH: 45
<212> TYPE: PRT
<213> ORGANISM: Homo sapiens

<400> SEQUENCE: 2

Met Arg Asp Gly Gly Gly Arg Gly Pro Glu Pro Leu Ser Ala Pro Val
1               5                   10                  15

Ser Ser Arg Gly Gly Ser Ala Leu Gly Glu Pro Ala Gly Leu Arg Arg
            20                  25                  30

Arg Gln Arg Arg Arg Phe Ser Pro Pro Leu Arg Leu Phe
        35                  40                  45

<210> SEQ ID NO 3
<211> LENGTH: 20
<212> TYPE: RNA
<213> ORGANISM: Artificial Sequence

```
<220> FEATURE:
<223> OTHER INFORMATION: Synthetic construct guide RNA

<400> SEQUENCE: 3
agcgccugug agcagccgcg                                                   20

<210> SEQ ID NO 4
<211> LENGTH: 20
<212> TYPE: RNA
<213> ORGANISM: Artificial Sequence
<220> FEATURE:
<223> OTHER INFORMATION: Synthetic construct guide RNA

<400> SEQUENCE: 4
caggccggcc ggcuccccga                                                   20

<210> SEQ ID NO 5
<211> LENGTH: 46
<212> TYPE: PRT
<213> ORGANISM: Mus musculus

<400> SEQUENCE: 5
```

Met Arg Asp Gly Gly Gly Arg Gly Pro Glu Pro Leu Ser Ala Pro Val
 1               5                  10                  15

Ser Ser Arg Gly Gly Ser Ala Leu Arg Glu Pro Ala Gly Leu Arg Arg
                20                  25                  30

Arg Gln Arg Arg Arg Phe Ser Pro Pro Leu Arg Leu Leu Phe
                35                  40                  45

```
<210> SEQ ID NO 6
<211> LENGTH: 45
<212> TYPE: PRT
<213> ORGANISM: Sus scrofa

<400> SEQUENCE: 6
```

Met Arg Asp Gly Gly Gly Arg Ser Pro Asp Pro Leu Ser Ala Pro Val
 1               5                  10                  15

Ser Ser Arg Gly Gly Ser Ala Leu Gly Glu Pro Ala Gly Arg Arg Arg
                20                  25                  30

Arg Gln Arg Arg Arg Phe Ser Pro Pro Leu Arg Leu Phe
                35                  40                  45

```
<210> SEQ ID NO 7
<211> LENGTH: 46
<212> TYPE: PRT
<213> ORGANISM: Bos taurus

<400> SEQUENCE: 7
```

Met Arg Asp Gly Gly Gly Arg Gly Pro Glu Pro Leu Ser Thr Pro Val
 1               5                  10                  15

Ser Ser Arg Gly Gly Ser Ala Leu Gly Glu Pro Ala Gly Arg Arg Arg
                20                  25                  30

Arg Gln Arg Arg Arg Phe Ser Pro Pro Leu Arg Pro Leu Phe
                35                  40                  45

```
<210> SEQ ID NO 8
<211> LENGTH: 45
<212> TYPE: PRT
<213> ORGANISM: Oryctolagus cuniculus

<400> SEQUENCE: 8
```

Met Arg Asp Gly Gly Gly His Gly Pro Glu Pro Leu Ser Ala Pro Val

```
                1               5                   10                  15
Ser Ser Arg Gly Gly Ser Ala Leu Gly Glu Pro Ala Gly Arg Arg
                    20                  25                  30

Arg Gln Arg Arg Arg Ala Ser Pro Pro Arg Arg Leu Phe
                    35                  40              45

<210> SEQ ID NO 9
<211> LENGTH: 46
<212> TYPE: PRT
<213> ORGANISM: Artificial Sequence
<220> FEATURE:
<223> OTHER INFORMATION: Synthetic construct consensus sequence
<220> FEATURE:
<221> NAME/KEY: MISC_FEATURE
<222> LOCATION: (7)..(7)
<223> OTHER INFORMATION: Xaa corresponds to His or Arg
<220> FEATURE:
<221> NAME/KEY: MISC_FEATURE
<222> LOCATION: (8)..(8)
<223> OTHER INFORMATION: Xaa corresponds to Gly or Ser
<220> FEATURE:
<221> NAME/KEY: MISC_FEATURE
<222> LOCATION: (10)..(10)
<223> OTHER INFORMATION: Xaa corresponds to Glu or Asp
<220> FEATURE:
<221> NAME/KEY: MISC_FEATURE
<222> LOCATION: (14)..(14)
<223> OTHER INFORMATION: Xaa corresponds to Ala or Thr
<220> FEATURE:
<221> NAME/KEY: MISC_FEATURE
<222> LOCATION: (25)..(25)
<223> OTHER INFORMATION: Xaa corresponds to Gly or Arg
<220> FEATURE:
<221> NAME/KEY: MISC_FEATURE
<222> LOCATION: (30)..(30)
<223> OTHER INFORMATION: Xaa corresponds to Leu or Arg
<220> FEATURE:
<221> NAME/KEY: MISC_FEATURE
<222> LOCATION: (38)..(38)
<223> OTHER INFORMATION: Xaa corresponds to Ala or Phe
<220> FEATURE:
<221> NAME/KEY: MISC_FEATURE
<222> LOCATION: (42)..(42)
<223> OTHER INFORMATION: Xaa corresponds to Leu or Arg
<220> FEATURE:
<221> NAME/KEY: MISC_FEATURE
<222> LOCATION: (44)..(44)
<223> OTHER INFORMATION: Xaa corresponds to Pro, Leu, or no amino acid

<400> SEQUENCE: 9

Met Arg Asp Gly Gly Gly Xaa Xaa Pro Xaa Pro Leu Ser Xaa Pro Val
1               5                   10                  15

Ser Ser Arg Gly Gly Ser Ala Leu Xaa Glu Pro Ala Gly Xaa Arg Arg
                    20                  25                  30

Arg Gln Arg Arg Arg Xaa Ser Pro Pro Xaa Arg Xaa Leu Phe
                    35                  40              45

<210> SEQ ID NO 10
<211> LENGTH: 57
<212> TYPE: DNA
<213> ORGANISM: Artificial Sequence
<220> FEATURE:
<223> OTHER INFORMATION: Synthetic construct pSin-EF2-puro-oligo

<400> SEQUENCE: 10
aattgggatc cccggacgaa ttcttcgaac atatgaagct tgctagcact agtgatc      57

<210> SEQ ID NO 11
<211> LENGTH: 53
<212> TYPE: DNA
```

<210> SEQ ID NO 11
<211> LENGTH: 53
<212> TYPE: DNA
<213> ORGANISM: Artificial Sequence
<220> FEATURE:
<223> OTHER INFORMATION: Synthetic construct pSin-EF2-puro-oligo

<400> SEQUENCE: 11
aattgggatc cccggacgaa ttcttcgaac atatgaagct tgctagcact agt         53

<210> SEQ ID NO 12
<211> LENGTH: 53
<212> TYPE: DNA
<213> ORGANISM: Artificial Sequence
<220> FEATURE:
<223> OTHER INFORMATION: Synthetic construct pSin-EF2-puro-oligo

<400> SEQUENCE: 12
gatcactagt gctagcaagc ttcatatgtt cgaagaattc gtccggggat ccc         53

<210> SEQ ID NO 13
<211> LENGTH: 15
<212> TYPE: PRT
<213> ORGANISM: Artificial Sequence
<220> FEATURE:
<223> OTHER INFORMATION: Synthetic construct of PTEN-45aa

<400> SEQUENCE: 13

Met Arg Asp Gly Gly Gly Arg Gly Pro Glu Pro Leu Ser Ala Pro
1               5                   10                  15

USE OF UPSTREAM OPEN READING FRAME 45aa-uORF NUCLEOTIDE SEQUENCE OF PTEN GENE AND POLYPEPTIDE CODED BY 45aa-uORF

BACKGROUND OF THE INVENTION

Technical Field

The present invention belongs to the field of bio-medicine and particularly relates to applications of an upstream Open Reading Frame (uORF) of a Phosphatase and Tensin homolog (PTEN) gene and a protein coded by the uORF.

Background Art

Malignancies in the Central Nervous System (CNS) are one type of tumors with the worst prognosis in all human tumors, resulting in the most years of potential life lost (up to about 20 years) among tumors (Rouse et al., 2016). Among those, the most common is Malignant Gliomas (MGs) with an incidence being 7.2/10 thousand people per year (Sturm et al., 2014). The gliomas have been classified into WHO grade I to grade IV according to histological patterns, wherein the grade IV is also called as Glioblastoma Multiforme (GBM) (Louis et al., 2016a), which accounts for more than half of the MGs with an extremely poor prognosis. The median survival time of patients, event after being treated by the most timely and effective surgeries and chemoradiotherapy, is only 12.1-14.6 months, and only 3-5% of patients can survive longer than 3 years (Krex et al., 2007). Since the current treatments still cannot significantly improve the survival time of patients, it has become a major focus in the field of glioma research at present to discover and clarify the development and progression mechanism of gliomas. We are looking forward to providing new ideas for clinical treatment and lay the foundation for the development of effective therapeutic regimens by revealing the development and progression mechanism of gliomas.

The exact pathogenesis of neurogliomas remains unknown, but great progress has been made in the past ten years on genetic and epigenetic researches of gliomas, which has pointed out the direction for the etiologic research of gliomas. A number of large multi-platform researches found that several mutant genes and the abnormalities of cell signaling pathways were associated with the occurrence and development of malignant gliomas (Cancer Genome Atlas Research, 2008; Ceccarelli et al., 2016; Parsons et al., 2008; Polivka et, 2016). The most important genetic and epigenetic abnormalities occur in the following signaling pathways: 1) Kirsten rat sarcoma viral oncogene homolog (KRAS) and Phosphoinositide 3-kinase (PI3K) carcinogenic pathways (accounting for 88% of GBMs); 2) p53 pathway (accounting for 87% of GBMs); 3) cell cycle regulation pathway (accounting for 78% of GBMs); and 4) changes in a number of newly discovered metabolic pathways, including Isocitrate Dehydrogenase 1/2 (IDH1/2) mutation (accounting for 10% of GBMs). The IDH1/2 mutation has become an important independent prognostic factor in one GBM, which has been strongly recommended as an important reference index for the clinical treatment of gliomas in the latest CNS tumor WHO classification (Louis et al., 2016b; Polivka et al., 2014; Xia et al., 2015).

The coding gene PTEN of Phosphatase and Tensin homolog (PTEN) is located on the chromosome 10q23.3 and is one of the most common genes that are down-regulated because of deletion or mutation in various human tumors (such as brain cancer, breast cancer, prostate cancer) (Li et al., 1997). As a tumor suppressor gene, the PTEN plays an important role in regulating cell growth, invasion, apoptosis, DNA damage repair and tumor cell resistance to chemoradiotherapy (Dean et al., 2005; Koul, 2008; Mellinghoff et al., 2005; Ming and He, 2012; Ortega-Molina and Serrano, 2013). The deletion of PTEN expression is considered as an early event in the development of gliomas, and PTEN mutation occurs in 60% of GBMs, which is the most common gene change (Bianco et al., 2003; Srividya et al., 2011). The PTEN mainly functions as a negative regulation factor for PI3K/Akt pathway. In contrast to PI3K, the PTEN takes effects to transform PIP3 into PI-4,5-P2 by dephosphorylation and to suppress all downstream signaling pathways regulated by Akt by reducing the activation of the Akt (Trotman et al., 2006). Previous studies have shown that in gliomas, the activation of the PI3K/Akt pathway directly affects the grade malignancy of gliomas and plays a key role in the development and progression process of GBMs (Rodriguez et al., 2011; Sonoda et al., 2001). Although previous studies have shown that the tumor suppressor gene PTEN plays an important regulatory role in gliomas, the exact mechanism thereof is still unclear. Therefore, it is of great significance for revealing the development and progression of gliomas according to discover all the active variants of the PTEN in gliomas and explore the tumor suppression mechanism thereof.

"Translation" is restricted to be only in protein-coding open reading frames (ORFs) in the traditional concept. With the development and progress of high-throughput deep sequencing and protein mass spectrometry, this concept is being changed by new research results. The researchers found that there were many small open reading frames (smORFs) in some regions of mammalian cells that were previously thought to be unable to code proteins, which could code peptides of less than 100 amino acids and had important biological functions (Andrews and Rothnagel, 2014; Chu et al., 2015; Slavoff, 2). 014). These regions include the 5'UTR non-coding region uORF (upstream ORF) and the 3'UTR non-coding region dORF (downstream ORF) of a coding gene mRNA, as well as some ncRNAs (non-coding RNAs) that were previously thought to be incapable of coding. Although some progress on smORFs has been made in researches of other species (Zanet et al., 2016), research on smORFs in human cancer is still blank at present.

In 2013, Science magazine reported that a lengthened PTEN protein PTEN-long that was translated by the 5'UTR non-coding region upstream of the tumor suppressor gene PTEN with the CTG as the starting codon, which was 173 amino acids more than the PTEN. Identical to the PTEN, the PTEN-long also has the phosphatase activity, and the PTEN-long can be secreted by cells and then enter other cells to take effect in cancer suppression (Hopkins et al., 2013). In 2014, researchers further found that the PTEN-long could induce the activity of cytochrome C oxidase in the process of mitochondrial metabolism, thus inducing the production of ATP in mitochondria (Liang et al., 2014). As early as 2003, it was found that the proliferation and cycle of cells both were significantly suppressed and blocked after the 5'UTR region of the PTEN gene was independently transferred in tumor cells (Han et al., 2003). Due to the limited technical conditions at that time, the researchers believed that it was activity difference caused by different lengths of promoters in the 5'UTR region of the PTEN.

BRIEF SUMMARY OF THE INVENTION

According to the present invention, there is found an open reading frame of 138 bases in the 5'UTR region of human PTEN gene (NCBI No.: NM_000314), which is named 45aa-uORF and can code an oligopeptide of 45 amino acids that is named PTEN-45aa (FIG. 1). The molecular weight of this oligopeptide is approximately 5 KD. The 45aa-uORF has the nucleotide sequence of SEQ ID NO: 1. The PTEN-45aa has the amino acid sequence of SEQ ID NO: 2.

In some embodiments, the present disclosure relates to nucleic acid molecules encoding PTEN-45aa molecules. The present disclosure provides, for example, nucleic acid molecules encoding the sequence of SEQ ID NO: 2, and provides nucleic acid molecules encoding variants, and modified forms, of SEQ ID NO: 2.

In other embodiments, the present disclosure relates to PTEN-45aa molecules. The present disclosure provides, for example, polypeptides comprising, consisting essentially of, or consisting of, the sequence of SEQ ID NO: 2; and provides variants, and modified forms, of polypeptides comprising, consisting essentially of, or consisting of, the sequence of SEQ ID NO: 2.

In further embodiments, antibodies that specifically bind to PTEN-45aa molecules are provided, as are nucleic acid probes that specifically bind to 45aa-uORF sequences.

In some embodiments, the present disclosure relates to methods for treating diseases. The present disclosure provides, for example, methods for treating tumors, such as PTEN regulated-related tumors. The present disclosure provides, for example, methods of treating tumors through administering nucleic acid molecules encoding PTEN-45aa molecules, and/or administering PTEN-45aa molecules.

The present disclosure further relates to detecting and/or determining whether a tumor is a PTEN-regulated tumor. In some embodiments, where a tumor in a subject, or a tumor sample from a subject, is detected and/or determined to be a PTEN-regulated tumor, the subject is treated with a nucleic acid encoding a PTEN-45aa molecule, and/or is treated with a PTEN-45aa peptide molecules.

DETAILED DESCRIPTION OF THE INVENTION

Figure 1:
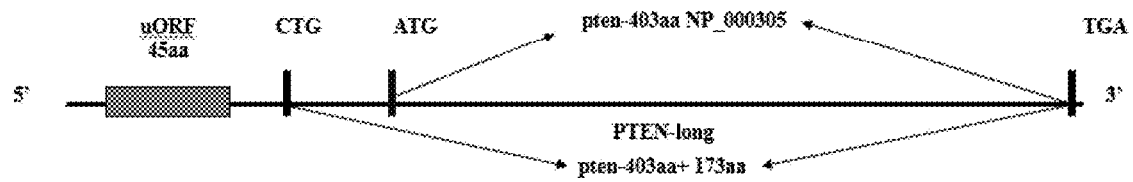
FIG. 1 illustrates a location diagram of 45aa-uORF on PTEN mRNA.

In some embodiments, the present disclosure relates to nucleic acid molecules encoding PTEN-45aa molecules. The present disclosure provides, for example, nucleic acid molecules encoding the sequence of SEQ ID NO: 2, and provides nucleic acid molecules encoding variants, and modified forms, of SEQ ID NO: 2. In one embodiment, the nucleic acid is a 45aa-uORF having the nucleotide sequence of SEQ ID NO: 1.

In some embodiments, the 45aa-uORF is a nucleic acid that is at least 90%, at least 91%, at least 92%, at least 93%, at least 94%, at least 95%, at least 96%, at least 97%, at least 98%, or at least 99% identical to any of the nucleic acids set forth as SEQ ID NO: 1.

In some embodiments, the nucleic acid encoding the PTEN-45aa molecule is a nucleic acid that has the sequence of SEQ ID NO: 1 except that it contains at least one substitution, addition, and/or deletion modification. It may contain, for example, at least 1, at least 2, at least 3, at least 4, at least 5, at least 10, at least 15, at least 25, or at least 50, substitution, addition, and/or deletion modifications.

In some embodiments, the nucleic acid encoding the PTEN-45aa molecule consists of, or consists essentially of, the sequence of SEQ ID NO: 1.

In certain embodiments, a nucleic acid sequence encoding the PTEN-45aa molecule is present within a vector. In some embodiments, the vector may be configured for in vitro or in vivo expression of the nucleic acid sequence encoding the PTEN-45aa molecule. The vector may contain, for example, one or more sequences that are heterologous to the nucleic acid sequence encoding the PTEN-45aa molecule, such as, for example, sequences encoding a selectable marker (such as a drug resistance gene, a fluorescent protein gene, a lacZ gene, and the like). Such vectors may also contain one or more expression control sequences, such as promoter and enhancer sequences, an IRES sequence, a polyadenylation sequence, and/or a termination sequence, for example. The promoter may be, for example, a tissue- or cell-specific promoter, and/or be an inducible or a constitutive promoter.

In some embodiments, the PTEN-45aa is a amino acid that is at least 90%, at least 91%, at least 92%, at least 93%, at least 94%, at least 95%, at least 96%, at least 97%, at least 98%, or at least 99% identical to any of the amino acids set forth as SEQ ID NO: 2.

In one aspect, the present invention provides a nucleic acid fragment 45aa-uORF or a polypeptide PTEN-45aa coded by the same.

In some embodiments, the PTEN-45aa molecule has the sequence of SEQ ID NO: 2 except that it contains at least one substitution, addition, and/or deletion modification. It may contain, for example, at least 1, at least 2, at least 3, at least 4, at least 5, at least 10, or at least 15 substitution, addition, and/or deletion modifications.

Comparisons of the 45aa-uORF coded micropeptide of human with sequences of other species revealed homologs in other species, including mouse, pig, cow, and rabbit (SEQ ID NOs: 5-8). The comparisons suggest that the 45aa-uORF coded micropeptide with a consensus sequence of MRDGGGX$_1$X$_2$PX$_3$PLSX$_4$PVSSRGGSALXEPAGX$_6$RR-RQRRRX$_7$SPPX$_8$RX$_9$LF (SEQ ID NO: 9), wherein: X$_1$ corresponds to H or R: X$_2$ corresponds to G or S: X$_3$ corresponds to E or D; X$_4$ corresponds to A or T: X$_5$ corresponds to G or R: X$_6$ corresponds to L or R: X$_7$ corresponds to A or F; X$_8$ corresponds to L or R: X$_9$ corresponds to P or no amino acids.

In another aspect, the present invention provides application of an upstream open reading frame 45aa-uORF nucleotide sequence of the PTEN gene or a nucleotide sequence for coding an equal amino acid sequence with the same or a polypeptide PTEN-45aa coded by the same in preparing drugs for treating or preventing tumors.

In another aspect, the present invention also provides application of a detection reagent for 45aa-uORF or a polypeptide PTEN-45aa coded by the same in preparing a reagent for tumor diagnosis and/or prognosis. Preferably, the reagent for tumor diagnosis and/or prognosis comprises: a probe for detecting the 45aa-uORF, or a primer for amplifying the 45aa-uORF, or an antibody against the PTEN-45aa.

In some embodiments, PTEN-45aa molecules are detectable with an antibody. The antibody may be a monoclonal antibody, a polyclonal antibody, a multivalent antibody, a multispecific antibody (e.g., bispecific antibody), and/or an antibody fragment that specifically binds to a PTEN-45aa molecule. The antibody may be a chimeric antibody, a humanized antibody, a CDR-grafted antibody, or a human antibody, for example. The antibody fragment may be, for example, a Fab, Fab', F(ab')2, Fv, Fd, single chain Fv (scFv), disulfide bond Fv (sdFv), or a VL or a VH domain. The antibody may be in the form of a conjugate, for example, conjugated to a tag, a detectable label, or a cytotoxic agent. The antibody may be of the isotype IgG (e.g., IgG1, IgG2, IgG3 or IgG4), IgA, IgM, IgE or IgD).

In another aspect, the present invention also provides a pharmaceutical composition for treatment or prevention of tumors. The pharmaceutical composition contains a 45aa-uORF nucleotide sequence of the PTEN gene, or a nucleotide sequence for coding an equal amino acid sequence with the same, or a polypeptide PTEN-45aa coded by the same. Optionally, the pharmaceutical composition may also comprise one or more medicinal pharmaceutical, or pharmaceutical carriers such as lentivirus and the like.

The present disclosure also relates to methods for treating tumors. The tumor may be a solid tumor or a blood tumor, and may be a tumor in which PTEN regulates the PI3K/Akt pathway. In some embodiments, the tumor may be a tumor in which PTEN is down-regulated, mutated, or deleted, and/or a tumor in which 45aa-uORF is down-regulated, mutated, or deleted.

Preferably, the tumor is brain cancer, liver cancer, colorectal cancer, bladder cancer, breast cancer, cervical cancer, prostate cancer, glioma, melanoma, pancreatic cancer, nasopharyngeal carcinoma, lung cancer, or gastric cancer. In some embodiments, the tumor is brain cancer, breast cancer, or prostate cancer. In certain embodiments, the tumor is neuroglioma.

Compositions containing a nucleic acid sequence encoding a PTEN-45aa molecule, or containing a PTEN-45aa peptide molecule, may be administered once a week, or several times (e.g., 2, 3, 4, 5, 6, 7, 8, 9 or 10) a week. The compositions may be administered for one or several weeks (1, 2, 3, 4, 5, 6, 7, 8, 9, or 10), for a month, or even for several months (2, 3, 4, 5, 6, 7, 8, 9, 10, 11 or 12 or more). In some instances, treatment may be continued for a year or for several years.

In some embodiments, compositions containing a nucleic acid sequence encoding a PTEN-45aa molecule, or containing a PTEN-45aa peptide molecule, are administered in conjunction with additional anti-tumor therapies. For example, the subject may be further treated with a chemotherapeutic drug (such as an alkylating agent, an antimetabolite, an anti-mitotic, an alkaloid, a taxane, a topoisomerase inhibitor, a cytotoxic antibiotic, or a combination thereof), radiation, or surgery. In some embodiments, the chemotherapeutic agent is selected from carmustine, fotemustine, lomustine and temozolomide. The subject may also be treated with an antibody therapy, such as bevacizumab.

In another aspect, the present invention also provides a kit for tumor diagnosis and/or prognosis. The kit contains: a probe for detecting the 45aa-uORF, or a primer for amplifying the 45aa-uORF, or an antibody against PTEN-45aa.

In some embodiments, the expression level (and/or the sequence) of the 45aa-uORF is determined for a tumor from a subject, and compared to that of a control sample. The control sample may be, for example, non-tumor cells, tumor cells in which PTEN is not down-regulated, mutated, or deleted; or tumor cells in which 45aa-uORF expression is known not to be down-regulated, mutated, or deleted. In some embodiments, the control cells are normal brain glial cells. In additional embodiments, subjects specifically determined to have tumors in which PTEN is down-regulated, mutated, or deleted; and/or in which 45aa-uORF expression is down-regulated; mutated, or deleted, are then specifically selected for treatment with one or more treatment methods described herein.

In another aspect, the present invention also provides an expression vector for coding PTEN-45aa and a host cell for expressing the vector as well as uses thereof in tumor suppression/prevention/treatment.

Figure 6:
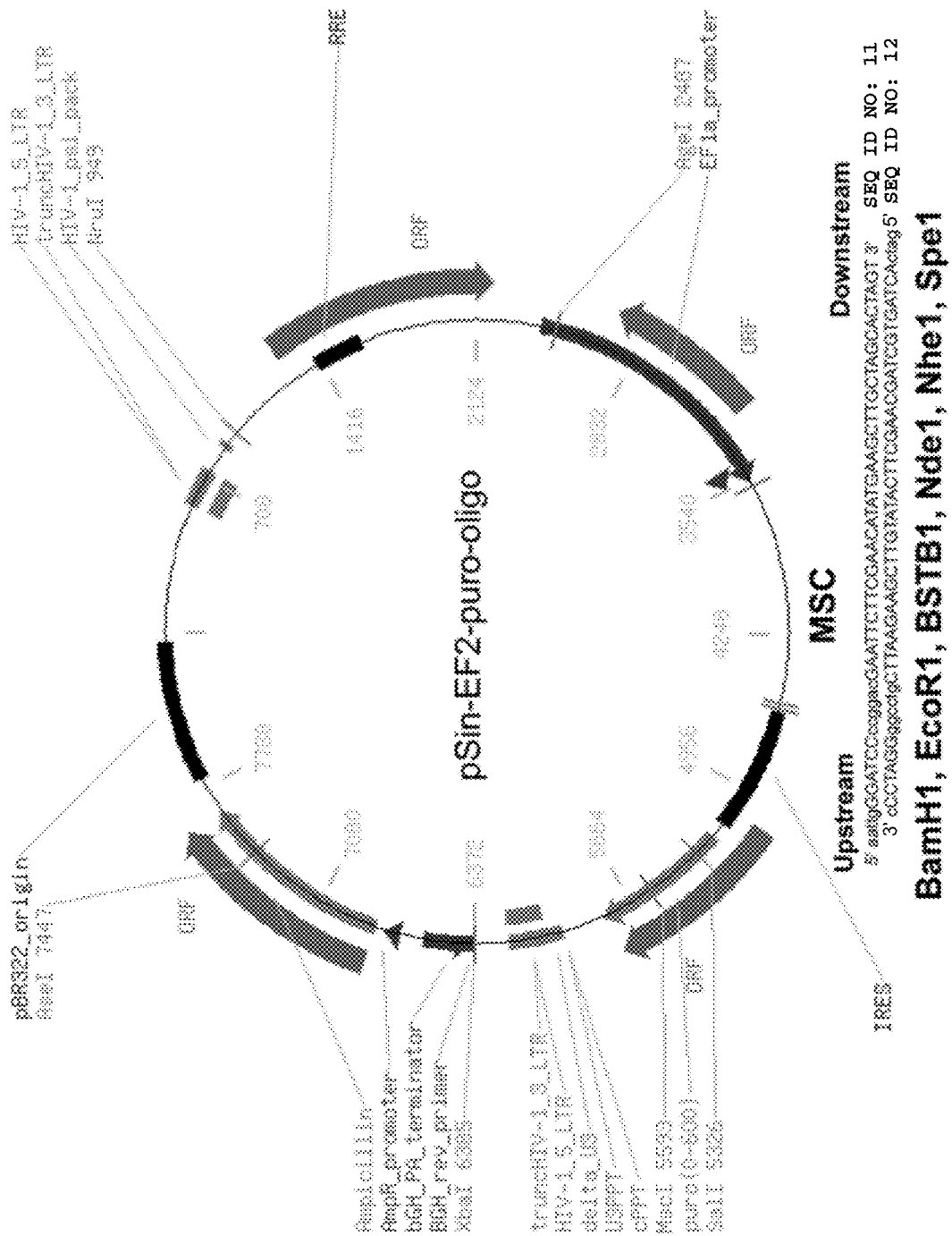
FIG. 6 illustrates the structure of the pSin-E2F-puro-oligo.

Polynucleotides 45aa-uORF of the present invention are inserted into expression vectors (i.e., a nucleic acid construct) to enable expression of the recombinant polypeptide. In one embodiment, the expression vector of the present invention includes additional sequences which render this vector suitable for replication and integration in eukaryotes. In one embodiment, the expression vector of the present invention includes a shuttle vector which renders this vector suitable for replication and integration in eukaryotes. In some embodiments, cloning vectors comprise transcription and translation initiation sequences (e.g., promoters, enhancers) and transcription and translation terminators (e.g., polyadenylation signals). In some embodiments, the vector used in the present invention is p-Sin-E2F-puro-oligo or pCDH-CMV-MCS-EF1-Puro. The structure of the p-Sin-E2F-puro-oligo is showed in FIG. 6.

In another aspect, the present invention also provides a polypeptide synthesized chemically or produced by recombinant expression, which has the amino acid sequence shown as SEQ ID NO: 2, or at least 90%, at least 91%, at least 92%, at least 93%, at least 94%, at least 95%, at least 96%, at least 97%, at least 98%, or at least 99% identical to any of the amino acids set forth as SEQ ID NO: 2. It has been proved by experiments that polypeptides, whether synthesized chemically or produced by recombinant expression, have the function of suppressing tumor. The tumor is PTEN regulation-related tumor. The PTEN regulation is particularly that the PTEN is involved in negative regulation of PI3K/Akt pathway. The tumor is preferably glioma, and more preferably, neuroglioma.

As discussed herein, the tumor is PTEN regulation-related tumor.

Alternatively, the tumor is brain cancer, breast cancer, prostate cancer. More preferably, the tumor is neuroglioma.

The PTEN gene is one of the most common genes that are down-regulated due to deletion or mutation in various human tumors (such as brain cancer, breast cancer, prostate cancer) (Li et al., 1997). As a tumor suppressor gene, the PTEN plays an important role in regulating cell growth, invasion, apoptosis, DNA damage repair and tumor cell resistance to chemoradiotherapy. An up-stream Open Reading Frame (uORF) can regulate expression of a gene downstream thereof. Therefore, it can be inferred that the uORF (45aa-uORF) of the PTEN and the polypeptide (PTEN-45aa) coded by the same in the present invention may play a regulatory role in the PTEN regulation related diseases and thus play a role in tumor suppression.

Therein, the PTEN regulation is particularly that the PTEN is involved in negative regulation of PI3K/Akt pathway. The PTEN can transform PIP3 into PI-4,5-P2 by dephosphorylation and suppress all downstream signaling pathways regulated by Akt by reducing the activation of the Akt (Trotman et al., 2006). In gliomas, the activation of the PI3K/Akt pathway directly affects the grade malignancy of gliomas and plays a key role in the development and progression process of GBMs (Rodriguez et al., 2011; Sonoda et al., 2001). Therefore, the PTEN is considered as an important suppressor for tumors by negatively regulating the Phosphatidylinositol 3-kinase (PI3K) signaling pathway.

Figure 2:
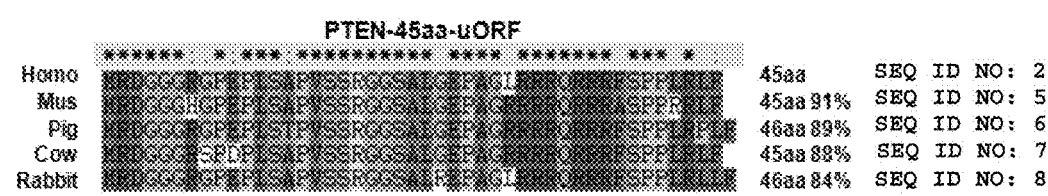
FIG. 2 illustrates prediction and endogenous expression identification;
A: diagram of location of 45aa-uORF on PTEN mRNA;
B: analysis of homology of 45aa-uORF coded micro-peptide in different species;
C: western detection of endogenous expression of 45aa-uORF in cells by specific antibody of 45aa-uORF coded micro-peptide.
Figure 2:
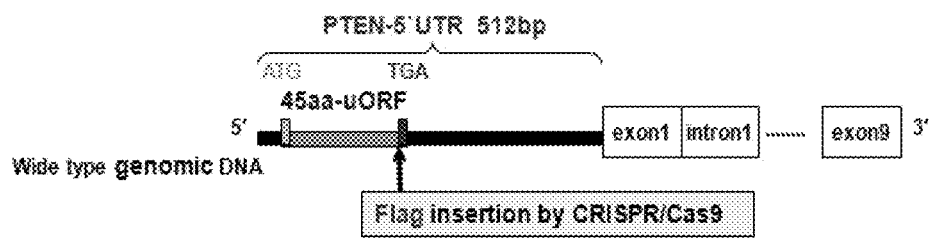
Figure 2:
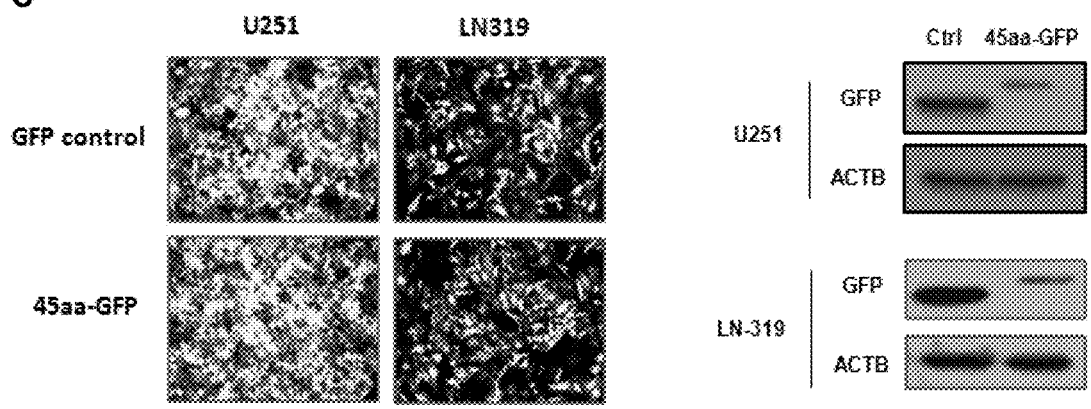

In one aspect, we have detected and identified the uORF coded micropeptide in 293 and U251 cells by preparing a PTEN-45aa specific antibody. Meanwhile, it also has been found that the expression quantity of the micropeptide in normal brain glial cells is much higher than that in glioma cells (FIG. 2).

Figure 3:
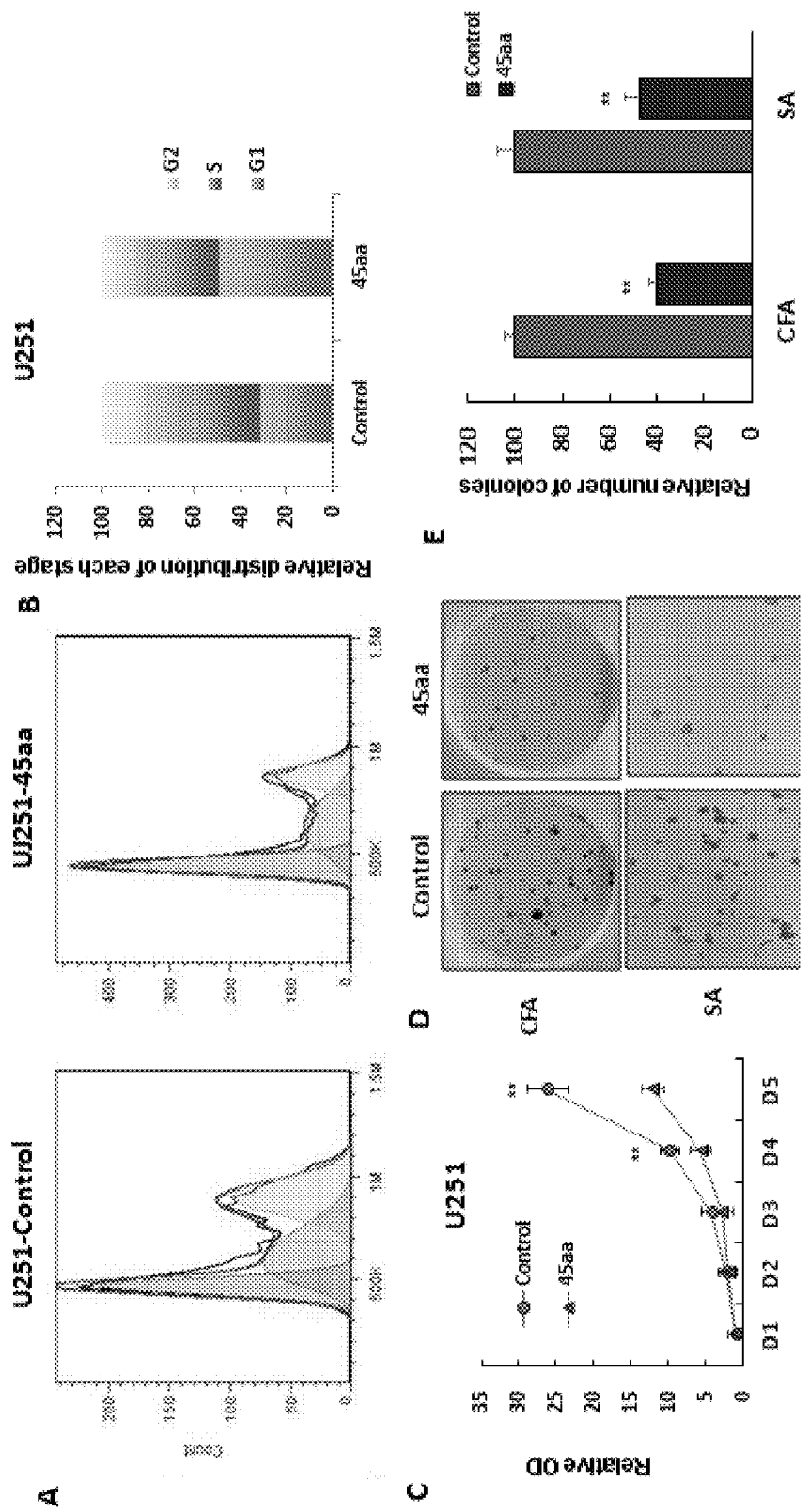
FIG. 3 illustrates that 45aa-uORF plays a role as a cancer suppressor polypeptide in glioma U251 cells;
A: the cell cycles of U251 cells that over-expressed 45aa-uORF detected by flow cytometry;
B: the statistical histogram of A, wherein the histogram indicates G2 (DNA postsynthetic phase), S (DNA synthesis phase), G1 (DNA presynthetic stage) sequentially from top to bottom;
C: measurement of changes of the growth curve by detection of the OD value of the CCK-8;
D: detection of the colony forming ability of cells by Clone Formation Assay (CFA) and Soft Agar (SA);
E: quantification of CFA and soft agar.

In one aspect, according to the present invention, an overexpression lentivirus vector is constructed based on the base sequence of the 45aa-uORF; the overexpression lentivirus vector is packaged and then employed to infect U251 neuroglioma cells; and then a glioma cell line of stably overexpressed 45aa-uORF coded micropeptide is obtained by screening, and then verified on cellular biological functions thereof. In the U251 neuroglioma cells, the overexpressed 45aa-uORF coded micropeptide can significantly suppress the growth, proliferation and clone formation of the U251 neuroglioma cells (FIG. 3).

In one aspect, the synthetic 45aa-uORF coded micropeptide can enter the U251 neuroglioma cells and can significantly suppress the growth and proliferation of the U251 neuroglioma cells.

Figure 5:
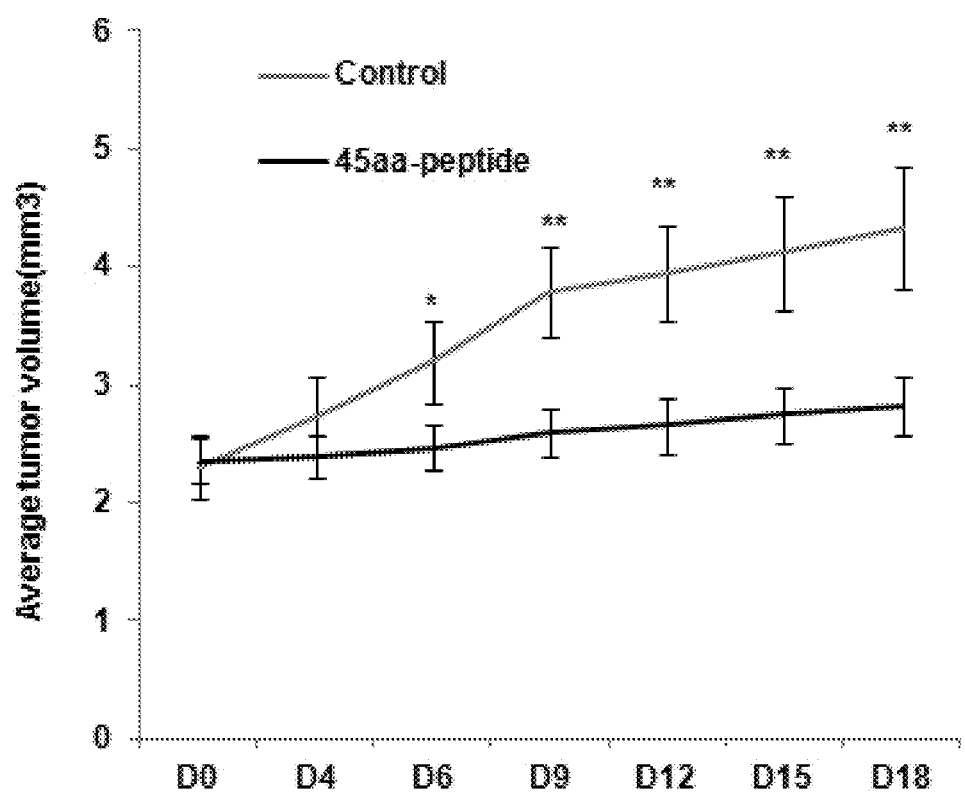
FIG. 5 illustrates that the chemically synthesized 45aa-uORF coded polypeptide can significantly suppress the growth of the U251 tumor subcutaneously implanted in nude mice.

In one aspect, the anti-tumor ability of the 45aa-uORF coded micropeptide is verified in vivo by animal experiments in the present invention. Mice are subcutaneously inoculated with 2 million U251 neuroglioma cells. Thirty days later, transplanted tumors are treated with the chemically synthesized 45aa-uORF coded micropeptide (25 ug/tumor) every other day. It is found that compared with a control polypeptide (the control polypeptide is synthesized by randomly shuffling the sequence of the 45aa-uORF coded polypeptide), the chemically synthesized 45aa-uORF coded micropeptide can significantly suppress the growth and formation of the U251 neuroglioma transplanted tumors, which indicating that the 45aa-uORF coded micropeptide also exhibits excellent anti-tumor activity at the animal level (FIG. 5).

In addition to the polypeptide having the amino acid sequence of SEQ ID NO: 2 as described above, other polypeptides conventionally modified by the sequence of the present invention should also be construed as having the tumor suppression function as described herein, such as an amino acid sequence that is at least 80%, at least 85%, at least 90%, at least 91%, at least 92%, at least 93%, at least 94%, at least 95%, at least 96%, at least 97%, at least 98%, or at least 99% similar with SEQ ID NO: 2 . . . . A polypeptide therapeutic agent may have a short circulation half-life period, proteolytic degradation and low solubility. In order to improve the pharmacokinetic and pharmacokinetic characteristics of biological pharmaceuticals of the present invention, such methods can be implemented: manipulating amino acid sequences to reduce or improve the immunogenicity and reduce proteolysis; fusing or coupling the peptide to immune globulins and serum proteins, such as albumin; and also incorporating biological pharmaceuticals (such as peptide of the present invention) and antibodies into drug delivery vectors for biological pharmaceuticals, so as to protect and slow down in release of biological pharmaceuticals and antibodies. Furthermore, it is envisaged to couple the peptide to natural or synthetic polymers. Specifically, for coupling with the synthetic polymers, pegylation or acylation, such as N-acylation, S-acylation, amidation and the like, is also envisaged.

In some embodiments, the PTEN-45aa peptide may be conjugated to one or more high molecular weight compounds to improve its properties. For example, it may be conjugated to polyethylene glycol, albumin, dextran, polyoxyethylene, styrene-maleic acid copolymer, polyvinylpyrrolidone, pyran copolymer, hydroxypropylmethacrylamide, and the like, to improve stability against various chemical, physical or biological factors, to prolong the half life in vivo, and/or to reduce immunogenicity.

PTEN-45aa molecules may also be prepared in the form of fusion proteins, containing a heterologous fusion sequence or partner. The fusion sequence may include, for example, an affinity tag sequence, such as a poly-histidine, myc-peptide or a FLAG tag. Such tags may be removed after isolation by methods known to one skilled in the art.

As used herein, "pharmaceutical excipients or pharmaceutical carriers" include any and all solvents, dispersion mediums, coatings, antibacterial and antifungal agents, isotonic agents, absorption retardants, and the like. Uses of such mediums and reagents in pharmaceutical active substances are well known in the art. Unless any conventional medium or agent is incompatible with active components, the use thereof in therapeutic compositions can be expected. Supplementary active ingredients can also be incorporated into the compositions. Pharmaceutical compositions containing a nucleotide sequence encoding a PTEN-45aa molecule, or containing a PTEN-45aa peptide, may contain one or more additional components such as carriers, excipients, diluents, pharmaceutically-acceptable carriers, stabilizers, buffering agents, preservatives, non-ionic detergents, antioxidants, and other additives. In certain embodiments, the additional components stabilize and extend the useable life of the composition, and/or prevent degradation, such as with stabilizers and preservatives. Other components may improve other properties such as solubility, reducing aggregation, and the like.

Preferably, the present invention provides a pharmaceutical composition comprising DMSO (dimethylsulfoxide) and polypeptide PTEN-45aa. As an embodiment, in the stock solution of the pharmaceutical composition, the concentration of polypeptide PTEN-45aa in DMSO is at least 20

μg/mL, and when the pharmaceutical composition is administered, the stock solution was diluted by solvent to the concentration of polypeptide PTEN-45aa in DMSO is at least 5 μg/mL, wherein the solvent is saline or PBS. The pharmaceutical composition can be administered to a patient by a variety of routes such as orally, transdermally, subcutaneously, intranasally, intravenously, intramuscularly, intrathecally, topically or locally. Typically, the pharmaceutical compositions will be administered orally, parenterally, intravenously or subcutaneously. According to the administration route, the active components may need to be coated with a material to be protected against the effects of enzymes, acids and other natural conditions that may inactivate the components.

The dose of the pharmaceutical composition to be administered to the subject can be adjusted based on the need and the characteristics of the individual subject. Exemplary dose ranges are from 0.01 mg/kg to 100 mg/kg, 0.01 mg/kg to 50 mg/kg, 0.1 mg/kg to 30 mg/kg and 1 mg/kg to 30 mg/kg, per dose, or per day. In one embodiment, an effective amount of polypeptide PTEN-45aa is higher than 5 mg/kg, preferably greater than 10 mg/kg, and still preferably greater than 15 mg/kg.

The present invention has the following beneficial effects:

1. According to the present invention, the small upstream open reading frame 45aa-uORF (45aa-uORF) is found in the 5' terminal of the PTEN for the first time, which can code a short peptide (PTEN-45aa) with 45 amino acids. By preparing the antibody against the PTEN-45aa, the 45aa-uORF can really be endogenously expressed in glioma cells and normal glial cells. At the same time, it is found, by detecting the expression quantities of a various of glioma samples and normal samples, that the expression quantity of the 45aa-uORF in the glioma tissue samples is significantly reduced as compared with that in normal brain tissue.

2. More excitingly, whether in in-vitro experiments or in living animal experiments, the polypeptide (PTEN-45aa), regardless of being produced by recombinant expression or synthesized artificially, can significantly suppress the growth and proliferation of glioma cells.

3. The present invention also provides a polypeptide synthesized artificially or expressed by a recombination vector. The micropeptide is particularly low in molecular weight, thus can easily enter glioma cells and penetrate to tumor tissue, and can also well penetrate through the blood brain barrier to treat neurogliomas.

4. The invention can provide a new peptide drug and new ideas and strategies for tumor treatment, in particular clinical treatment or prevention of neurogliomas, based on the newly discovered upstream open reading frame (45aa-uORF) and the micropeptide (PTEN-45aa) coded by the same.

Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

The following terms, unless otherwise indicated, shall be understood to have the following meanings:

As used herein, the term "nucleic acid" or "nucleic acid fragment" refers to a polymeric form of nucleotides of at least 10 bases in length. The term includes DNA molecules (e.g., cDNA or genomic or synthetic DNA) and RNA molecules (e.g., mRNA or synthetic RNA molecules), as well as analogs of DNA or RNA containing non-natural nucleotide analogs, non-native internucleotide bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. And, such "nucleic acid" or "nucleic acid fragment" may comprise modified nucleotides as a percentage of the total number of nucleotides present in the nucleic acid molecule, such as at least about 5%, 10%, 15%, 20%, 25%, 30%, 35%, 40%, 45%, 50%, 55%, 60%, 65%, 70%, 75%, 80%, 85%, 90%, 95% or 100% modified nucleotides).

The term "expression vectors" as used herein is intended to refer to a nucleic acid molecule capable of directing the expression of nucleic acid sequences to which they are operatively linked. One type of expression vectors is a "plasmid", which refers to a circular double stranded DNA loop into which additional DNA segments may be ligated. Other expression vectors include cosmids, bacterial artificial chromosomes (BAC) and yeast artificial chromosomes (YAC). Another preferred type of expression vectors is a viral vector, wherein additional DNA segments may be ligated into a viral genome that is usually modified to delete one or more viral genes. Certain vectors are capable of autonomous replication in a host cell into which they are introduced (e.g., vectors having an origin of replication which functions in the host cell). Other expression vectors can be integrated stably into the genome of a host cell upon introduction into the host cell, and are thereby replicated along with the host genome. Preferred viral vectors include retroviral and lentiviral vectors.

The term "overexpression" as used herein with reference to a nucleic acid sequence refers to a higher level of transcription and/or translation of a nucleic acid or protein product encoded by a nucleic acid sequence in a cell. Overexpression is most commonly accomplished by operative linkage of nucleic acid sequences to a strong promoter/enhancer sequence which stimulates transcription in the target host cell, or construction of lentivirus that containing the target nucleic acid sequence transfected host cell. (i.e., a constitutive "on" signal) or regulated (i.e., the "on" signal is induced or repressed by another signal or molecule within the cell).

The terms "polypeptide", "micropeptide" and "short peptide" should be construed as having the same meaning to express an amino acid fragment, encompassing both naturally-occurring and non-naturally-occurring proteins, and fragments, mutants, derivatives and analogs thereof, and may be monomeric or polymeric. The terms as used herein encompasses analogs and mimetics that mimic structural and thus biological function.

The terms "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

The terms "pharmaceutical carriers" refers to a carrier or a diluent that does not cause significant irritation to an organism and does not abrogate the biological activity and properties of the administered compound. Examples of suitable pharmaceutical carriers are well known in the art and include phosphate buffered saline solutions, water, emulsions, such as oil/water emulsions, various types of wetting agents, sterile solutions, etc. Pharmaceutical composition comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently.

The compositions of the invention may be administered locally or systematically. Administration will generally be parenterally, e.g., intravenously; DNA may also be administered directed to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present invention might comprise proteinaceous carriers, like, e.g., serum albumine or immunoglobuline, preferably of human origin. Furthermore, it is envisaged that the pharmaceutical composition of the invention might comprise further biologically active agents, depending on the intended use of the pharmaceutical composition.

In the present invention the various nucleotide sequences and vectors of the invention are administered either alone or in any combination using standard vectors and/or gene delivery systems, and optionally together with a pharmaceutically acceptable carrier or excipient. Subsequent to administration, said polynucleotides or vectors may be stably integrated into the genome of the subject.

On the other hand, viral vectors may be used which are specific for certain cells or tissues and persist in said cells. Suitable pharmaceutical carriers and excipients are well known in the art. The pharmaceutical compositions prepared according to the invention can be used for the prevention or treatment or delaying of different kinds of diseases, which are related to PTEN regulation-related tumor.

Furthermore, it is possible to use a pharmaceutical composition of the invention which comprises polynucleotide or vector of the invention in gene therapy. Suitable gene delivery systems may include liposomes, receptor-mediated delivery systems, naked DNA, and viral vectors such as herpes viruses, retroviruses, adenoviruses, and adeno-associated viruses, among others. Delivery of nucleic acids to a specific site in the body for gene therapy may also be accomplished using a biolistic delivery system, such as that described by Williams (Proc. Natl. Acad. Sci. USA 88 (1991), 2726-2729). Further methods for the delivery of nucleic acids comprise particle-mediated gene transfer as, e.g., described in Verma, Gene Ther. 15 (1998), 692-699.

Example 1 Endogenous Expression and Identification of 45Aa-uORF Coded Micro-Peptide By using ORF Finder (website: bioinformatics.org/sms/orf_find.html), an Open Reading Frame (ORF) of 138 nt was found in the 5'UTR of the first intron region of PTEN mRNA (NM_000314). The ORF could code an oligopeptide of 45 amino acids and was named 45aa-uORF by us, and the oligopeptide coded by the ORF was named PTEN-45aa. With protein molecular weight prediction software (website: bio-soft.net/sms/prot_mw.html), the molecular weight of the oligopeptide was predicted to be about 5 KD. A polyclonal antibody capable of specifically recognizing this micro-peptide and detectable by western blot assay was designed according to the amino acid sequence of the 45aa-uORF. The specific method was as follows: by means of chemical polypeptide synthesis, one amino acid sequence segment MRDGGGRGPEPLSAP (SEQ ID NO: 13) of the 45aa-uORF was synthesized as an immunogen for injection into and immunization of a New Zealand white rabbit, and then a target antibody was purified to detect the 45aa-uORF coded micro-peptide in cells. One segment of the 45aa-uORF was specifically knocked out from the genome using CRISPR/Cas9 to silence the expression of the 45aa-uORF micro-peptide at the genomic level, thereby obtaining 45aa-uORF knocked-out 293 cell line. The endogenous expression and change of the 45aa micro-peptide were detected by western with the 45aa-uORF specific antibody.

```
SEQ ID NO: 1
homo-45aa-uORF (138nt) nucleotide sequence
                                          (SEQ ID NO: 1)
ATGAGAGACGGCGGCGGCCGCGGCCCGGAGCCCCTCTCAGCGCCTG
TGAGCAGCCGCGGGGGCAGCGCCCTCGGGGAGCCGGCCGGCCTGCG
GCGGCGGCAGCGGCGGCGTTTCTCGCCTCCTCTTCGTCTTTTCTAA SEQ ID NO: 2
homo-45aa-uORF coded amino acid sequence (PTEN-
45aa)
                                          (SEQ ID NO: 2)
MRDGGGRGPEPLSAPVSSRGGSALGEPAGLRRRQRRRFSPPLRLF
```

Details of the Method

1) Establishment of CRISPR/Cas9 Knockout Cell Line

A number of gRNA sequences were designed according to the sequence of the 45aa-uORF and targeted to different regions of the 45aa-uORF, respectively, and one segment of the 45aa-uORF was specifically eliminated to obtain a cell line with the 45aa-uORF being genomically knocked out.

Detailed information of the gRNA sequences are shown below:

```
SEQ ID NO: 3
45aa-cas9/gRNA-1:
                                         (SEQ ID NO: 3)
5'-AGCGCCUGUGAGCAGCCGCG-3'

SEQ ID NO: 4
45aa-cas9/gRNA-2:
                                         (SEQ ID NO: 4)
5'-CAGGCCGGCCGGCUCCCCGA-3'
```

(the 5'-terminal was added with g when cloning to facilitate efficient promotion of hU6 promoter.)

HEK293T cells were transiently transfected with pX330-Puro-PTEN-SgRNA plasmid, and the efficiency of transfection was detected by sequencing. The result showed that 45aa-SgRNA2 was a high efficiency SgRNA. The 45aa-SgRNA2 plasmid was selected for the follow-up experiment and used to transfect HEK293 cells. The HEK293 cells transfected with 45aa-SgRNA2 were screened using puromycin and the positive clones were picked out. After DNA sequencing, the clones with frameshift mutation of the PTEN-45aa sequence in the cloned daughter cells could meet the requirements. Thus, the cell line with the 45aa-uORF being genomically knocked out was obtained.

2) Cell Culture

HEK-293T cells were purchased from ATCC (ATCC® CRL-11268™), cultured in DMEM (Gibco, 8113281) medium containing 10% Fetal Bovine Serum (FBS, Gibco, 10099) and 10 U/mL penicillin-streptomycin (Gibco, 15140-122), and placed in a constant-temperature moist incubator with 5% CO2 at 37° C. The cells were passaged every three days with a passage ratio of 1:4.

3) Western Blot

The total protein of cells was extracted with RAPA, and the extracted protein was quantified by BCA protein assay; 5% SDS-PAGE spacer gel and 15% SDS-PAGE separating gel were disposed, and the total protein of the loaded sample was 100 micrograms. Protein electrophoresis was run at 80V for 20 minutes and at 150V for 1 hour. Protein was transferred to a Membrane at 100V for 2 hours. 5% skim milk was used for sealing for 1 hour. Rabbit anti-45aa-uORF antibody (1:500)), B-actin antibody (Abcam No. ab197345) (1:3000) were incubated at 4 DEG C. overnight. In the next day, rabbit secondary antibody (1:10000) was incubated at normal temperature for 1 hour; TBST was used for washing for 5 times, each for 5 minutes, and then lighting, developing and fixing were carried out.

Experimental Results

By preparing the 45aa-uORF specific antibody, we detected and identified the real existence of the uORF coded micropeptide in the cells (FIG. 2). Meanwhile, it was also found that the expression quantity of the micropeptide in normal brain glial cells was much higher than that in glioma cells, suggesting that the micropeptide might have the tumor suppression function (FIG. 2).

Example 2 Determination of Biological Functions of 45Aa-uORF Micro-Peptide

1) Establishment of Overexpressed 45Aa-uORF Stable Cell Line Overexpressing 45Aa-uORF A vector for overexpressed 45Aa-uORF-GFP (the skeleton of the vector is pCDH-CMV-MCS-EF1-Puro) was constructed and then used to transfect into HEK-293T cells together with lentivirus skeleton vectors PSPAX2, PMD2G in a ratio of 1:3:1 to package the lentivirus. The medium supernatants with the lentivirus were collected at 48 hours and 72 hours, respectively, and then used to infect U251 cells (added with 8 μg/ml polybrene to improve the infection efficiency). Puromycin (1 mg/mL) was employed for screening and removed three days later, and then the cells were proliferated normally. Steps of cell transfection include: inoculating 0.5 million 293T cells into a 6-well culture plate, and performing transfection after cell adherence to the wall in 24 hours; before transfection, preparing 100 μL serum-free medium DMEM and plasmid into a mixed liquid; uniformly mixing 100 μL serum-free medium DMEM with 5 μL (2 ug plasmid/5 μL lipo2000) liop2000 liposome into a liposome mixed liquid; mixing the two mixed liquids in equal proportions and standing at room temperature for 20 minutes; operating according to the operating instructions of the transfection reagent; with the final volume in the wells of the 6-well plate being 1 ml, performing transfection for 6 hours, and then replacing with 1 ml normal medium (10% fetal bovine serum added with 1% DMEM medium and 1% penicillin-streptomycin) for cell culture under the conditions of 37 DEG C. and 5% carbon dioxide.

2) Flow Cytometry in Analysis of Cell Cycle 1.5 Million U251 glioma cells of lentivirus overexpressed 45aa-uORF were inoculated into a T25 culture flask. The cells were cultured for 24 hours continuous after being adhered to the wall in DMEM (Gibco, 8113281) containing 10% fetal bovine serum (FBS, Gibco, 10099) and 10 U/mL penicillin-streptomycin (Gibco, 15140-122) and placed in a constant-temperature moist incubator with 5% CO2 at 37° C. The cells were passaged every three days with a passage ratio of 1:4. Trypsinized cells were centrifuged and then washed with PBS once, and then centrifuged again to remove the supernatant; and the precipitate was resuspended in 1 mL PBS and then added dropwise with 3 mL 100% ethyl alcohol precooled at −20 DEG C. for cell fixation for 30 minutes. Then, after being centrifuged and washed with PBS once, the precipitate was resuspended in 25 μg/mL Propidium Iodide (PI, sigma)/PBS solution, stained for 30 minutes away from light, and then detected on cell-cycle distribution thereof.

3) Detection of Cell Proliferation with CCK-8

U251-GFP control cells or U251-45aa-uORF-GFP cells were inoculated into a 96-well plate in a quantity of 2000 cells per well. Each sample was repeated 5 times. After cell adherence to the wall, the CCK-8 (Dojindo, CK04) reagent was added by 10 μL per well every 24 hours for culture at 37° C. for 1-4 hours, and then the absorbance (OD) of 450 λm was detected. The absorbance value was directly proportional to the number of cells.

4) Clone Formation Assay (CFA)

U251-GFP control cells or U251-45aa-uORF-GFP cells were inoculated into a 6-well plate in a quantity of 2000 cells per well and continuously cultured in a constant-temperature moist incubator with 5% CO2 at 37° C. for two weeks. Then, a picture was taken after staining with crystal violet, and the number of the formed clones was determined. The assay was repeated at least three times.

5) Soft Agar Assay

Firstly, 2 mL 0.6% (prepared in DMEM) low-gelling temperature agarose was added to a 6-well plate, and after the agarose was coagulated, 2 mL 0.35% (prepared in DMEM) low-gelling temperature agarose containing 20000U251-GFP control cells or U251-45aa-uORF-GFP cells was added thereto and uniformly mixed by shaking slightly for continuous culture in a constant-temperature moist incubator with 5% CO2 at 37° C. for two weeks. Then, a picture was taken under an optical microscope and the number of the formed clones was determined. The assay was repeated at least three times.

Experimental Result

In U251 neuroglioma cells, the overexpressed 45aa-uORF coded micropeptide could significantly suppress the growth and proliferation of U251 glioma cells (FIG. 3).

Example 3 Verification of Ability of Micro-Peptide to Enter Cells

Figure 4:
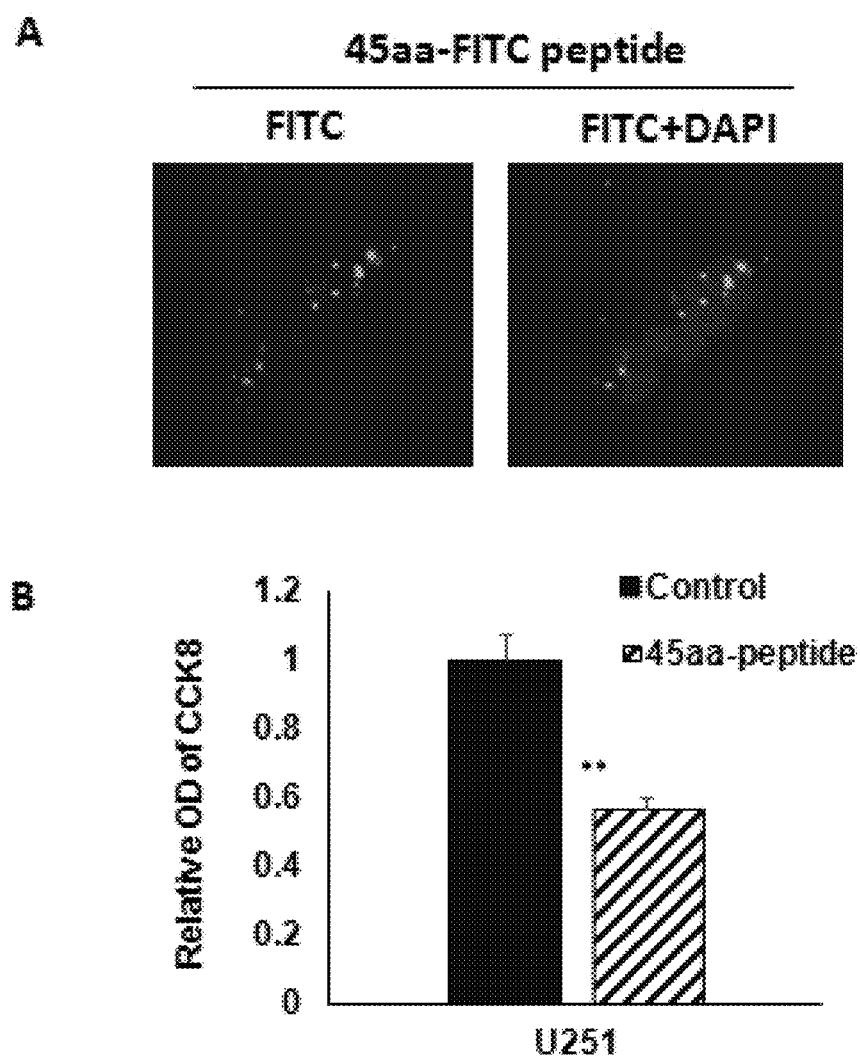
FIG. 4 illustrates that the chemically synthesized 45aa-uORF coded polypeptide can enter U251 cells and significantly suppress the growth of glioma cells;
A: adding 45 aa-peptide (concentration: 25 μM)=to U251 cells, washing out of the superfluous polypeptide using PBS 4 hours later, and detection of the ability of the polypeptide to enter cells by immunofluorescence;
B: continued cell culture for 72 hours and then detection of the cell viability with CCK-8.

U251 cells were inoculated onto a glass slide at the density of 50%, and different concentrations of PTEN-45aa micropeptide t attached with FITC fluorescent groups (the micropeptide was dissolved in DMSO with a concentration being 20 μg/μL) were added to treat cells for 4 hours, then fixed with Faure Marin, and observed and photographed under a fluorescence microscope. It was found that the PTEN-45aa micropeptide in the concentration of 20 μM could enter the U251 cells smoothly in 4 hours, and all cells in sight were fluorescent (FIG. 4).

Example 4 Verification of Tumor Suppression Function of 45Aa-uORF Micro-Peptide at the Animal Level U251 cells were inoculated to the left and right sides of nude mice by 2 million at each point. Thirty days later, the formation of tumors was observed, and the tumors were averagely divided into a control group and an experimental group by size (five nude mice and ten tumors in each group). The control group was injected with a control polypeptide every other day, and the experimental group was injected with the 45aa-uORF polypeptide every other day. Each tumor was injected with 25 μg synthetic peptide. The long diameters and short diameters of the tumors were measured before the medication, and after 5-6 times medications, the nude mice were sacrificed, and tumors were taken out, photographed and weighed.

Tumor volume=½*long diameter*the square of short diameter

The experimental results, as shown in FIG. 5, showed that the chemically synthesized 45aa-uORF coded micropeptide could significantly suppress the growth and formation of the tumors transplanted by glioma U251 as compared with the control polypeptide (the control polypeptide was synthesized by randomly shuffling the sequence of the 45aa-uORF coded polypeptide, indicating that the 45aa-uORF coded micropeptide also exhibited excellent anti-tumor activity at the animal level.

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "WANH-61861-Sequences_ST25.txt", created Aug. 21, 2023, file size of 8,192 bytes, is hereby incorporated by reference.

The invention claimed is:

1. A method for treating a glioma tumor in a subject in need thereof, comprising administering to the subject a therapeutically effective amount of a polypeptide, wherein the polypeptide consists of the amino acid sequence of SEQ ID NO: 2.

2. The method of claim 1, wherein the therapeutically effective amount is 0.01 mg/kg to 100 mg/kg per dose.

3. The method of claim 1, wherein the therapeutically effective amount is 0.01 mg/kg to 100 mg/kg per day.

* * * * *